(12) United States Patent
Galon et al.

(10) Patent No.: US 10,317,408 B2
(45) Date of Patent: Jun. 11, 2019

(54) METHOD FOR QUANTIFYING IMMUNE CELLS IN TUMORAL TISSUES AND ITS APPLICATIONS

(71) Applicants:INSERM (Institut National de la Sante et de la Recherche Medicale), Paris (FR); Universite Paris Descartes, Paris (FR); Assistance Publique-Hopitaux de Paris, Paris (FR)

(72) Inventors: Jerome Galon, Paris (FR); Franck Pages, Paris (FR); Bernhard Mlecnik, Paris (FR)

(73) Assignees: INSERM (Institut National de la Sante et de la Recherche Medicale), Paris (FR); Universite Paris Descartes, Paris (FR); Assistance Publique-Hopitaux de Paris, Paris (FR)

( * ) Notice: Subject to any disclaimer, the term of this patent is extended or adjusted under 35 U.S.C. 154(b) by 0 days.

(21) Appl. No.: 14/407,698

(22) PCT Filed: Jun. 14, 2013

(86) PCT No.: PCT/EP2013/062405
§ 371 (c)(1),
(2) Date: Dec. 12, 2014

(87) PCT Pub. No.: WO2013/186374
PCT Pub. Date: Dec. 19, 2013

(65) Prior Publication Data
US 2015/0153349 A1 Jun. 4, 2015

(30) Foreign Application Priority Data
Jun. 14, 2012 (WO) .................. PCT/IB2012/001446

(51) Int. Cl.
*G01N 33/574* (2006.01)
*G01N 33/50* (2006.01)

(52) U.S. Cl.
CPC ... *G01N 33/57492* (2013.01); *G01N 33/5047* (2013.01); *G01N 33/574* (2013.01); *G01N 2800/52* (2013.01)

(58) Field of Classification Search
CPC ......... G01N 33/57492; G01N 33/5047; G01N 33/574; G01N 2800/52
See application file for complete search history.

(56) References Cited

U.S. PATENT DOCUMENTS

2007/0140540 A1* 6/2007 McLaren ............... G01N 1/312 382/128
2007/0141711 A1* 6/2007 Stephens .................. G01N 1/06 436/43
2009/0215053 A1* 8/2009 Galon .............. G01N 33/57484 435/6.16

FOREIGN PATENT DOCUMENTS

WO 2007045996 A1 4/2007

OTHER PUBLICATIONS

Halama et al., "The Local Immunological Microenvironment in Colorectal Cancer as a Prognostic Factor for Treatment Decisions in the Clinic; The Way Ahead" Oncoimmunology, Jan. 1, 2012, vol. 1, No. 1, pp. 62-66.
Halama et al., "Quantification of Prognostic Immune Cell Markers in Colorectal Cancer Using Whole Slide Imaging Tumor Maps" Analytical and Quantitative Cytology and Histology, Dec. 2010, vol. 36, No. 6, p. 333-340.
Pages et al., "In Situ Cytotoxic and Memory T Cells Predict Outcome in Patients with Early-Stage Colorectal Cancer" Journal of Clinical Oncology, Dec. 10, 2009, vol. 27, No. 35, p. 5944-5951.
Halama et al., "Estimation of Immune Cell Densities in Immune Cell Conglomerates: An Approach High-Throughput Quantification", PLOS One, Nov. 2009, vol. 4, No. 11, p. 1-6.
Halama et al., "Localization and Density of Immune Cells in the Invasive Margin of Human Colorectal Cancer Liver Metastases are Prognostic for Response to Chemotherapy", Cancer Research, Aug. 16, 2011, vol. 71, No. 17, p. 5670-5677.

* cited by examiner

*Primary Examiner* — Andrea S Grossman
(74) *Attorney, Agent, or Firm* — W&C IP

(57) ABSTRACT

A method for assessment of a number or density of immune cells in tumoral tissues comprising the steps consisting in: a. providing one or more immunostained slices of tissue section obtained by an automated slide-staining system by using antibodies binding specifically to antigens (markers) expressed by immune cells. b. proceeding to digitalization of the slides of step a. by high resolution scan capture, whereby a high definition (4.6 µm/pixel or better) digital picture of the slide to be analyzed is obtained, c. detecting the slice of tissue section on the digital picture d. analyzing the slice of tissue section for defining (i) the tumor (CT) and (ii) the invasive margin of the tumor (IM), e. providing a size reference grid with uniformly distributed units having a same surface, said grid being adapted to the size of the tumor to be analyzed, e1. checking the quality of immunostaining, f. detecting and quantifying stained cells of each unit whereby the number or the density of immune cells stained of each unit is assessed.

16 Claims, 12 Drawing Sheets tumor region (CT)  Invasive margin (IM)

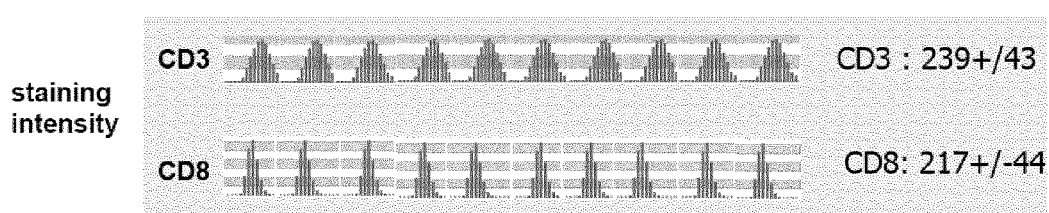
Fig. 16
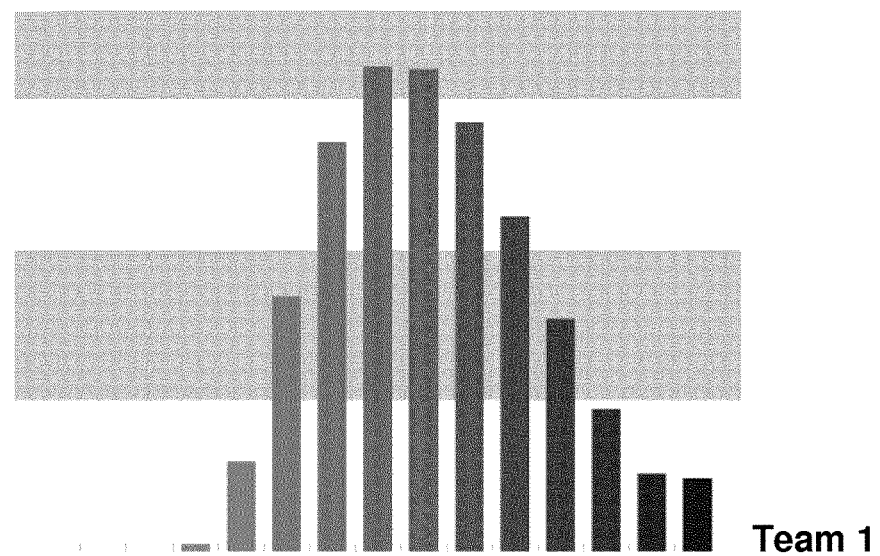
Fig. 17
Fig. 18

METHOD FOR QUANTIFYING IMMUNE CELLS IN TUMORAL TISSUES AND ITS APPLICATIONS

FIELD OF THE INVENTION

The present invention relates to a method for quantifying immune cells in tumoral tissues and its applications.

BACKGROUND OF THE INVENTION

EP-A-EP1943520 and WO2007045996 describe an in vitro method for the prognosis of patients for progression of a cancer and/or of the survival, and/or the prediction of response to treatment (chemotherapy, radiotherapy, biotherapy, immunotherapy) which method comprises the following steps:

a) quantifying, in a tumour tissue sample from said patient, at least one biological marker indicative of the status of the local adaptive immune reaction of said patient; and b) comparing the value obtained at step a) for said at least one biological marker with a predetermined reference value for the same biological marker; which predetermined reference value is correlated with a specific prognosis of progression of said cancer or survival of said patient or prediction of treatment response (such as chemotherapy, radiotherapy, biotherapy, immunotherapy) to anticipate the "good responder" vs "bad responder".

The tumour tissue sample may be selected from the group consisting in (i) a global primary tumour (as a whole), (ii) a tissue sample from the tumour, (iii) a tissue sample from the tissue directly surrounding the tumour which tissue may be more specifically named the "invasive margin" of the tumour, (iv) lymphoid islets in close proximity with the tumour, (v) the lymph nodes located at the closest proximity of the tumour, (vi) a tumour biopsy performed prior surgery, and (vii) a distant metastasis.

The biological marker is preferably quantified, at step a), in tumour samples collected from two regions of the tumour, respectively (i) the tumour (CT) and (ii) the invasive margin of the tumour (IM).

The above method was implemented on tissue microarrays (TMAs). However, most of the steps of the process are implemented manually and problems with reproducibility of measurements might be observed. For example differences between pathologists for the selection of tumour areas to punch can occur, based on the Haematoxylin-Eosin counterstaining examination. In addition, a difficulty to punch exactly the area selected by the pathologist is observed. Such typical errors can occur at each step. Although the method described in these documents makes it possible to obtain high-performance for predicting the survival of patients with cancer, research is still going on into methods with even better qualities, particularly as regards automation reproducibility and comparability of the results.

As highlighted by Halama et al in Quantification of prognostic immune cell markers in colorectal cancer using whole slide imagining tumour maps, analytical and quantitative cytology and histology, Vol. 32, 6, December 2010, pp. 333-340, sampling histologic probes using tissue microarrays (TMAs) is especially problematic in the case of a spatial heterogeneity of the target molecule as it is frequently observed in cancer tissue. Halama et al proposes full tissue slide microscopy for data acquisition. However the study does not demonstrate a specific diagnostic algorithm producing a parameter able to interpret the spatial heterogeneity of the tumour. He concludes that until this diagnostic algorithm is created and a follow-up study is performed he cannot know if the tumour map will have prognostic value in a single patient.

SUMMARY OF THE INVENTION

Now the applicant has discovered a method for assessment of a number or density of immune cells in tumoral tissues, for obtaining an immune score (or immunoscore) of patients suffering of a cancer.

It has been noted in a surprising and unexpected fashion that the use of the new method for assessment of a number or density of immune cells in tumoral tissues ensures automation, repeatability and reproducibility of the method described in WO2007045996 and thus provides a standard test method for inter-laboratory tests for predicting the survival and treatment response of patients with cancer.

The new method has particularly fewer problems with repeatability and reproducibility when compared to the method of EP-A-EP1943520 and WO2007045996

DESCRIPTION OF THE PREFERRED EMBODIMENTS

A subject of the present application is therefore a method for assessment of a number or density of immune cells in tumoral tissues comprising the steps consisting in:

a. providing one or more immunostained slices of tissue section obtained by an automated slide-staining system by using antibodies binding specifically to antigens expressed by immune cells.

b. proceeding to digitalisation of the slides of step a. by high resolution scan capture, whereby a high definition (4.6 µm/pixel or better) digital picture of the slide to be analysed is obtained, c. detecting the slice of tissue section on the digital picture d. analyzing the slice of tissue section for defining (i) the tumour (CT) and (ii) the invasive margin of the tumour (IM), e. providing a size reference grid with uniformly distributed units having a same surface, said grid being adapted to the size of the tumour to be analyzed, f. detecting and quantifying stained cells of each unit whereby the number or the density of immune cells stained of each unit is assessed.

Typically, the antibodies are specific for a protein expressed by an immune cell and more particularly are specific for an immune cell surface marker. For example, the antibodies may be specific for a marker as described in WO2007045996, immune cells considered may be B cells and preferably T cells. For example, the T cells of the invention are T cells of sub groups CD3+ cells (T cells), CD8+ cells or GZMB+ cells (cytotoxic T cells), CD4+ cells (T helper cells), CD45RO+ cells (memory T cells). In a particular embodiment, the antibodies are specific for CD3, CD4, CD8, CD20, CD45RO, and GZMB markers.

When two or more markers are used, the above steps are preferably implemented separately for each marker. For example anti-CD3 antibodies are used for one slice of tissue and anti-CD8 antibodies for another slice of tissue, preferably an adjacent slice of tissue. A multiple, for example double, detection may alternatively be made when the antibodies used for detecting different markers are stained differently. One detectable signal is therefore available for each marker.

Immunohistochemistry or IHC refers to the conventional process of detecting antigens (generally, proteins) in cells of a tissue section by using the principle of antibodies binding specifically to antigens in biological tissues. Immunohistochemical staining allows visualising an antibody-antigen interaction. It can be implemented in a number of ways. In the most common instance, an antibody is conjugated to an enzyme, such as peroxidase, that can catalyse a colour-producing reaction. Alternatively, the antibody can also be tagged to a fluorophore, such as fluorescein or rhodamine.

Antibodies used in the invention are typically commercially available. In particular when CD3 marker is selected for implementing the method of the invention, 2GV6 antibody commercially available from Roche Ventana (Tucson, Ariz., USA) may be suitable (Chetty R, et al., J Pathol. 173(4): 303-307, 1994). In particular when CD8 marker is selected for implementing the method of the invention C8/144B antibody commercially available from Dako (Denmark) may be suitable (Mason D Y, Cordell J L, Gaulard P, Tse A G D, Brown M H. Immunohistological detection of human cytotoxic/suppressor T cells using antibodies to a CD8 peptide sequence. J Clin Pathol 1992:45:1084-8). Two or more markers can be detected when implementing the process. In a particular embodiment the following combinations may be used: CD3+CD8, CD3+CD45RO, CD3+CD20, CD3+GZMB, CD8+CD20, CD8+GZMB, CD8+CD45RO, CD20+GZMB, CD20+CD45RO, GZMB+CD45RO, CD4+CD8, CD4+CD45RO, CD4+GZMB, CD4+CD20, and all the combinations of 3 markers among the CD3, CD8, CD20, CD45RO, CD4 and GZMB markers. Under preferred conditions for implementing the invention, combinations CD3+CD45RO, CD8+CD45RO and CD3+CD8 are most preferred, more particularly the latter, because of low background staining obtained with these antibodies.

Tissue sections of different kinds of tumours may be used in the present process. A tumour tissue sample encompasses (i) a global primary tumour (as a whole), (ii) a tissue sample (a biopsy) from the tumour, (iii) a ressected tumour sample, and (iv) a distant metastasis sample.

One or more slides provided with a stained slice of tissue section—may be used in the present method. Usually one single slide is sufficient for one marker, unless a poor staining is obtained.

For example an IHC automate such as BenchMark® XT allowing automatic stained slide preparation may be used for implementing the immunohistochemical staining step a).

Digitalisation of the slides of step a. is made by scan capture, for example with a high resolution Hamamatsu NanoZoomer® 2.0-HT scanner allowing scanning standard-size (26 mm×76 mm) slides. This scanner provides high definition digital pictures (×20: 0.46 µm/pixel is preferred) and (×40: 0.23 µm/pixel).

The detection, i.e. the definition of the boundaries of the slice of tissue section on the digital picture may be man-made by a skilled technician, usually a medical doctor, or may be implemented by appropriate software.

Analyzing the slice of tissue section for defining the boundaries of (i) the tumour (CT) and (ii) the invasive margin of the tumour (IM) may also be man-made by a medical doctor, or may be implemented by appropriate software. Three areas are usually obtained corresponding to healthy tissue, tumour and invasive margin therebetween.

Preferably, before this step, the slice of tissue section is divided into areas of similar properties, according to criteria such as one or more of colors, intensity, compactness, emptiness, tissue density, nuclear density using counter-staining, granulosity, shape, size of detected elements and area.

At step e. a reference grid adapted to the size of the tumour to be analyzed is provided. A preferably hexagonal, square or rectangular meshed grid is used. A square meshed grid is particularly preferred.

The surface of an individual mesh, hereafter "unit", shall be for particularly of $100 \cdot 10^{-9}$ m$^2$ to $1000 \cdot 10^{-9}$ m$^2$, more particularly of $300 \cdot 10^{-9}$ m$^2$ to $800 \cdot 10^{-9}$ m$^2$, and very particularly of about $650 \cdot 10^{-9}$ m$^2$.

Hexagonal, square or rectangular units having a surface of $10 \cdot 10^{-9}$ m$^2$ to $1000 \cdot 10^{-9}$ m$^2$, particularly of $100 \cdot 10^{-9}$ m$^2$ to $1000 \cdot 10^{-9}$ m$^2$, more particularly of $300 \cdot 10^{-9}$ m$^2$ to $800 \cdot 10^{-9}$ m$^2$, and very particularly of about $650 \cdot 10^{-9}$ m$^2$ are preferred.

A square meshed reference grid having sides of 500 to 1000 µm in length, preferably about 800 µm, is most preferred because of the appropriate representative mean of immune cells in such area, in the range of 1 to 5000 cells.

A preferred reference grid is provided for example with 2 to 5000, preferably 10 to 2000, particularly 100 to 1000, more particularly 400 to 700 units.

A grid with 400 to 700 square shaped units having sides of about 800 µm in length is most preferred.

The units cover the whole surface of the sample.

The density of cells of interest may be expressed as the number of said cells of interest that are counted per unit of surface area of tissue sample, for example per mm$^2$. The density of cells of interest may also consist of the percentage of a specific cell subset (e.g. CD3+ T cells) per total cells or total cell subpopulation (set at 100%). Obtaining, at step g) of the method, more than one quantification value for each biological marker that is used allows a more accurate final cancer prognosis or prediction of a treatment response than when only one quantification value per biological marker is determined.

When the method for assessment of a number or density of immune cells in tumoral tissues is followed by further steps where the quality of staining may be an important parameter for the accuracy of the results obtained, it is important to check the quality of staining of the slice of tissue.

Therefore under preferred conditions for implementing the invention, the method further comprises a step e1. of checking the quality of staining of the slice of tissue.

Checking the quality of staining may be implemented by calculating, preferably with appropriate software, the distribution of the staining intensity of positive cells detected for each unit and for the total tumour region, representing said distribution.

The mean, median, min and max of the relevant (for example brown) staining intensity of all positive stained cells detected in the tumour regions may be calculated and provided for each slide analyzed.

The values and the distribution of the staining intensity can be compared to a reference (normal range intensity) determined for each marker.

In the detection step f., the number of positive cells of each unit is counted. Since the surface of each unit is known, the density of positive cells per surface unit is also known. Step f. may be man-made by a skilled technician, usually a medical doctor, or may be implemented by appropriate software. The method allows quantifying, in a tumour tissue sample from a patient, at least one biological marker indicative of the status of the immune reaction of said patient against cancer.

The above method may be used for segregating patients into groups according to their expected survival or to their response to a cancer treatment. The value hereabove may be compared, for each biological marker used, with a predetermined reference value for the same biological marker; which predetermined reference value is correlated with a specific prognosis of progression of said cancer and/or survival of the patient and/or response to a cancer treatment ("good responder" vs "bad responder").

The following parameters may be used for quantifying stained cells of each unit, for a given marker:
- total number of stained cells
- density of stained cells per surface unit
- total number of isolated stained cells (not in contact with other stained cells)
- total number of stained cells within a cluster of stained cells (where at least 1 stained cell is in contact with a min. of 3 stained cells).

Under preferred conditions for implementing the invention,
- each region (CT and IM) of a tumour is analyzed.
- the density of stained cells of each unit is determined.
- a colour is allocated to each unit according to the density of stained cells detected and according to a gradation, for example green to red (from minimum density to maximum density). These steps are preferably implemented by appropriate software.

Preferably the density of stained cells in each tumour region (CT and IM) is determined by the mean density of 1 to 1000 units, preferably 2 to 100 units, more preferably 3 to 10 units, most preferably 3 units, having maximum density. The selection of units having maximum density is preferably implemented by appropriate software. One value is obtained for each of the CT and IM areas. If the values are above a threshold value, the sample is considered as positive. Therefore for a single marker, four possibilities are possible: CT+ and IM+, CT− and IM−, CT+ and IM−, CT− and IM+. When two or more CD3, CD8, CD20, CD45RO, and GZMB markers are used, the same possibilities are possible for the second marker.

The inventors have found that the method is reliable if 30% or more, preferably 40% or more of the surface of a unit taken into account is filled with cells.

Criteria other than the mean density of several units are possible, based preferably on combinations of sub-criteria of groups A, B and C Group A
1. maximum number of positive cells (positive cells refers to stained cells detected by the software)
2. maximum density of positive cells
3. sum of the number of positive cells
4. sum of the surface of positive cells
5. sum of the densities of positive cells
6. mean number of positive cells
7. mean density of positive cells
8. maximum number of positive cells
9. median number of positive cells
10. median density of positive cells In group A, criteria 2, 5, 7 and 10 are preferred because they take into account the surface of tissue analyzed.

Group B
1. single positive cells
2. positive cells in clusters containing at least 3 positive cells
3. single positive cells or clusters containing at least 3 positive cells
4. all positive cells
5. most positive units, preferably three (3) positive units
6. random units, preferably three (3) random units.

In group B, criteria 4 and 5 are preferred because the criterion takes into account all positive cells detected, and reduces the heterogeneity by selecting the 3 most stained units. On the other side, using three to fifty random units allows obtaining very quick results since this procedure may avoid quantifying the whole tumour. The result of analysis of a stained slide is 10-100 times quicker.

Group C
1. tumour region CT
2. tumour region IM
3. tumour regions CT and IM

In group C, criterion 3: "tumour regions CT and IM" is preferred because this method is the most powerful in discriminating patients, and where the Hazard Ratio between the groups are the highest.

Examples of combinations of such criteria include for example for cells markers such as CD3:

| combinations of criteria | Group A | Group B | Group C |
| --- | --- | --- | --- |
| C1 | 7 | 4 | 3 |
| C2 | 7 | 5 | 3 |
| C3 | 10 | 4 | 3 |
| C4 | 10 | 5 | 3 |
| C5 | 6 | 4 | 3 |
| C6 | 6 | 5 | 3 |
| C7 | 9 | 4 | 3 |
| C8 | 9 | 5 | 3 |
| C9 | 4 | 4 | 3 |
| C10 | 4 | 5 | 3 |
| C11 | 3 | 4 | 3 |
| C12 | 3 | 5 | 3 |
| C13 | 5 | 4 | 3 |
| C14 | 5 | 5 | 3 |
| C15 | 7 | 4 | 2 |

Other examples of combinations of such criteria wherein the sub-criterion of group A is the median number of positive cells include for example 1—median number of positive cells (single cells or clusters containing at least 3 cells) in the units with a surface of tissue greater than or equal to 40% of the total surface of the unit in the tumour regions CT and IM 2—number of positive cells (single cells) in the units with a surface of tissue greater than or equal to 40% of the total surface of the unit in the tumour regions CT and IM, 3—median number of positive cells (in clusters containing at least 3 cells) in the units with a surface of tissue greater than or equal to 40% of the total surface of the unit in the tumour regions CT and IM, 4—median of the density of positive cells (single cells or clusters containing at least 3 cells) in the units with a surface of tissue greater than or equal to 40% of the total surface of the unit in the tumour regions CT and IM, 5—median of the sum of the number of positive cells (single cells or in clusters containing at least 3 cells) in the units with a surface of tissue greater than or equal to 40% of the total surface of the unit in the tumour regions CT and IM, 6—median of the sum of the number of positive cells (single cells) in the units with a surface of tissue greater than or equal to 40% of the total surface of the unit in the tumour regions CT and IM 7—median of the sum of the number of positive cells (in clusters containing at least 3 cells) in the units with a surface of tissue greater than or equal to 40% of the total surface of the unit in the tumour regions CT and IM 8—median of the sum of the density of positive cells (single cells or in clusters containing at least 3 cells) in the units with a surface of tissue greater than or equal to 40% of the total surface of the unit in the tumour regions CT and IM 9—median of the mean number of positive cells (single cells or in clusters containing at least 3 cells) in the units with a surface of tissue greater than or equal to 40% of the total surface of the unit in the tumour regions CT and IM 10—median of the mean number of positive cells (single cells) in the units with a surface of tissue greater than or equal to 40% of the total surface of the unit in the tumour regions CT and IM For each of the above combinations of criteria, and for each marker (e;g. CD3, CD4, CD8, CD20, CD45RO, or GZMB marker), a threshold value is determined allowing finding whether the sample is considered as positive or negative on this criterion.

A threshold value, for each marker in each region, for each method, is determined. The threshold value is determined using cohort of patient with said cancer, and taking an arbitrary threshold, the threshold for the mean or the median value of the cohort, or preferably using the optimal p-value discriminating the patients, or the optimal Hazard ratio discriminating the patients, or the optimal iAUC value discriminating the patients, For CD3 for example, suitable values are about:

| combinations of criteria N° | Value |
|---|---|
| C1 | 1232 |
| C2 | 463 |
| C3 | 368 |
| C4 | 2839. |
| C5 | 56198 |

These values are subject to changes according to the calibration adjustments of the software used such as signal intensity threshold or cell detection, and adjustments based on the type of patient analyzed (primary tumour, metastasis, the cancer stages I, II, III, IV, the tumour type studied (colon, breast, lung, melanoma, etc. . . . ).

Each reference threshold value for each marker may be predetermined by carrying out a method comprising the steps of:

m) providing at least one collection of tumour tissue samples selected from the group consisting of: i) a collection of tumour tissue samples from cancer patients conventionally classified as Tis, or T1, or T2, or T3 or T4 and N0, or N1, or N2, or N3 and M0 or M1, having undergone anti-cancer treatment, and subsequently having no cancer relapse or no cancer recurrence after the anti-cancer treatment; ii) a collection of tumour tissue samples from cancer patients conventionally classified as Tis, or T1, or T2, or T3 or T4 and N0, or N1, or N2, or N3 and M0 or M1, having undergone anti-cancer treatment, and subsequently having cancer relapses or recurrences after the anticancer treatment.

n), quantifying for each tumour tissue sample comprised in a collection of tumour tissue samples provided at step m), the said biological marker, whereby a collection of quantification values for the said biological marker and for the said collection of tumour tissue samples is obtained;

o) calculating, from the said collection of quantification values obtained at the end of step n), the mean quantification value for the said biological marker, whereby a predetermined reference value for said biological marker that is correlated with a specific cancer prognosis or a response to treatment is obtained. The "anti-cancer treatment" that is referred to in the definition of step m) above relate to any type of cancer therapy undergone by the cancer patients previously to collecting the tumour tissue samples, including radiotherapy, chemotherapy, biotherapy, immunotherapy and surgery, e.g. surgical resection of the tumour.

In view of a minimal statistical significance value, the threshold reference value may be a range of values. For example, on a hypothetical scale of 1 to 10, if the ideal threshold is 5, a suitable (exemplary) range may be from 4-6. Therefore, a patient may be assessed by comparing values where values greater than 5 indicate for example a good prognosis and values less than 5 indicate for example a poor prognosis; or a patient may be assessed by comparing values and comparing the values on a scale, where values above the range of 4-6 indicate for example a good prognosis and values below the range of 4-6 indicate for example a poor prognosis, with values falling within the range of 4-6 indicating an intermediate prognosis.

In certain preferred embodiments of step o) of the method for determining threshold values above, the said information relating to the actual clinical outcome of the patients are selected from the group consisting of (i) the duration of the disease-free survival (DFS) and (ii) the overall survival (OS).

For segregating patients into groups according to their expected survival, the availability of a predetermined reference value for more than one biological marker is preferred. Thus, generally, one or more predetermined reference value(s) is (are) determined for a plurality of biological markers indicative of the status of the immune response against cancer that are encompassed herein, by simply repeating any one of the methods for obtaining predetermined reference values that are described above, for the plurality of biological markers.

A preferred predetermined reference value consists of a median quantification value for the biological marker of interest that discriminates between bad cancer prognosis and good cancer prognosis.

The accuracy of a specific predetermined reference value increases with the number of tissue samples that are used for obtaining quantification values for a specific biological marker and thus for calculating a mean value (the predetermined reference value) which is associated with a specific cancer outcome. Preferably in view of obtaining highly relevant predetermined reference values for each biological marker of interest, the said predetermined reference values consist of the mean value of a plurality of quantification values of the said marker measured on tissue samples originating from the same plurality number of cancer-bearing patients which underwent a specific clinical outcome.

More preferably, for assessing accurate predetermined reference values, the reference values are predetermined from at least 50 quantification values, for a specific biological marker, thus using tissue samples originating from at least 50 cancer-bearing patients that have underwent a specific bad or good clinical outcome, e.g. DFS or OS of more than 5 years following diagnosis. In preferred embodiments, a predetermined reference value is obtained from at least, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500 or more quantification values for a specific biological marker.

Other embodiments for predetermining a reference value are disclosed in EP-A-EP1943520 and WO2007045996.

A most preferred method of the invention is a fully computorized method.

The above method may be implemented as follows:

A tumour tissue sample is prepared. The tumoral tissue sample is preferably fixed in formalin and embedded in a rigid fixative, such as paraffin (wax) or epoxy, which is placed in a mould and later hardened to produce a block which is readily cut. Thin slices of material are prepared using a microtome, placed on a glass slide and submitted to immunohistochemistry, for example using an IHC automate such as BenchMark® XT, for obtaining stained slides. If several markers are to be considered, different stained slides are prepared.

When the number or density of intratumoral immune cells of each unit has been assessed according to the above method, one of the above combinations of criteria is selected and a value is obtained for the marker or each marker. The value obtained is compared with the threshold/reference value of the marker and of the combination of criteria.

If the value obtained is above the threshold/reference value, the tumour is allotted a quotation such as "+" or "high", and if the value obtained is under the threshold/reference value, the tumour is allotted a quotation such as "−" or "low".

When implementing the above method with a single marker and considering separately the CT and the IM, the tumour and therefore the patient may be high/high, high/low, low/high, low/low. Three categories of patients may be obtained: "2 high", "1 high", "0 high". In such a case, an immune score (or immunoscore) from 0 to 2 may be obtained.

When implementing the above method with a two marker and considering either (and preferably) the CT or the IM, the tumour and therefore the patient may also be high/high, high/low, low/high, low/low. Three categories of patients may be obtained: "2 high", "1 high", "0 high". Also in such a case, an immune score (or immunoscore) from 0 to 2 may be obtained.

When implementing the above method with two markers and considering separately the CT and the IM, the tumour and therefore the patient may be high/high/high/high, low/low/low/low, high/high/high/low, high/high/low/low, and high/low/low/low. For the three latter, the assessment may be irrespective of the marker and of the positive area CT or IM.

Any convention may be used. For example "+", "positive", "high", "Hi" are equivalent for assessing the same result (many stained cells).

In such a case, an immune score (or immunoscore) in a 0 to 4 range may be summarized as follows:
Score 4: Four (4) "high" assessments
Score 3: Three (3) "high" assessments
Score 2: Two (2) "high" assessments
Score 1: One (1) "high" assessment
Score 0: Zero (0) "high" assessment.

The method according to the invention has advantageous properties because of their reproducibility, repeatability, and the possibility to perform the method in a routine practice.

The present process allows obtaining numerical values for the whole tumour if desired, and not only information limited to tissue microarrays (TMA).

The scope of the invention can be understood better by referring to the examples given below, the aim of which is to explain the advantages of the invention.

A subject of the present invention is also a kit for implementing the above method comprising a support comprising reference threshold values.

A further subject of the present invention is a computer provided with a software for implementing the above method.

Preferred conditions for implementing the methods described above also apply to the other subjects of the invention envisaged above, particularly the kits for implementing the said above methods.

DESCRIPTION OF THE DRAWINGS

FIG. 16 illustrates histograms for the percentage of distribution of the staining intensity for CD3 and CD8 for ten different units of a stained slice of tumour.

FIGS. 17-19 illustrate histograms representing the percentage of positive cells detected in CT and IM tumour regions with regards to staining intensity of the cells, after CD3 immunostaining.

Figure 1:
FIG. 1 represents a picture of a slice of tissue section detected on a digital picture.
Figure 2:
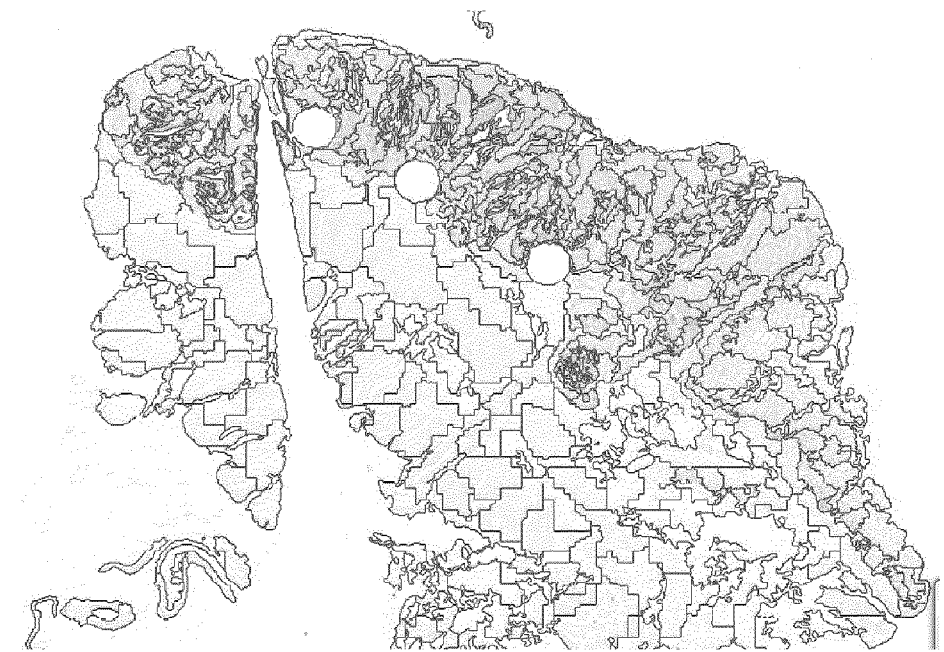
FIG. 2 shows the picture of a slice of tissue section of FIG. 1 divided into areas of similar properties, according to one or several criteria.
Figure 3:
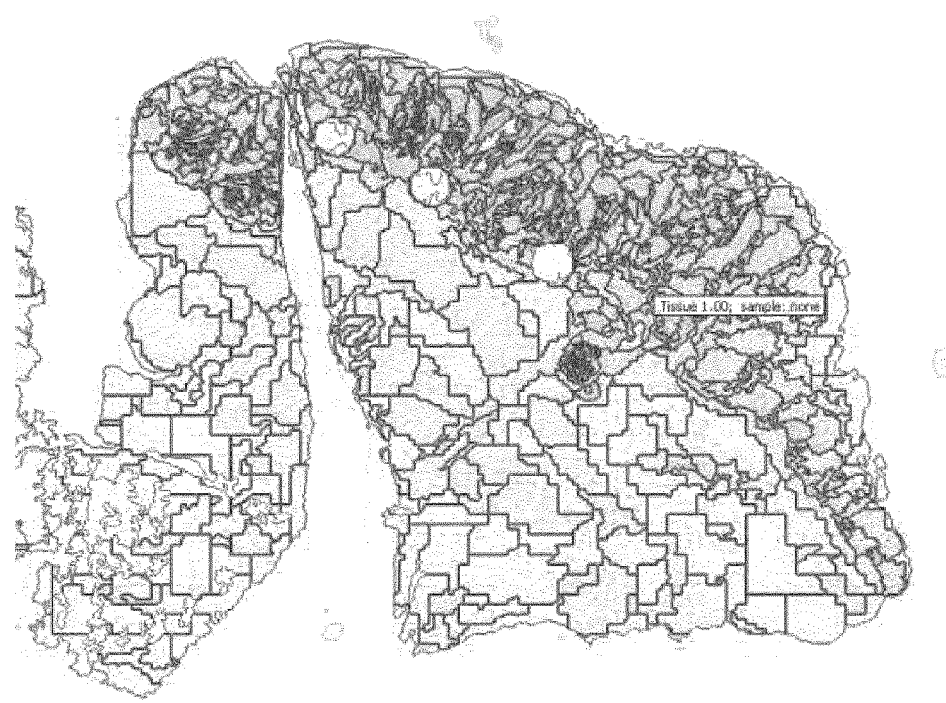
FIG. 3 is a picture similar to picture 2 wherein the tumour and the invasive margin of the tumour have been defined.
Figure 4:
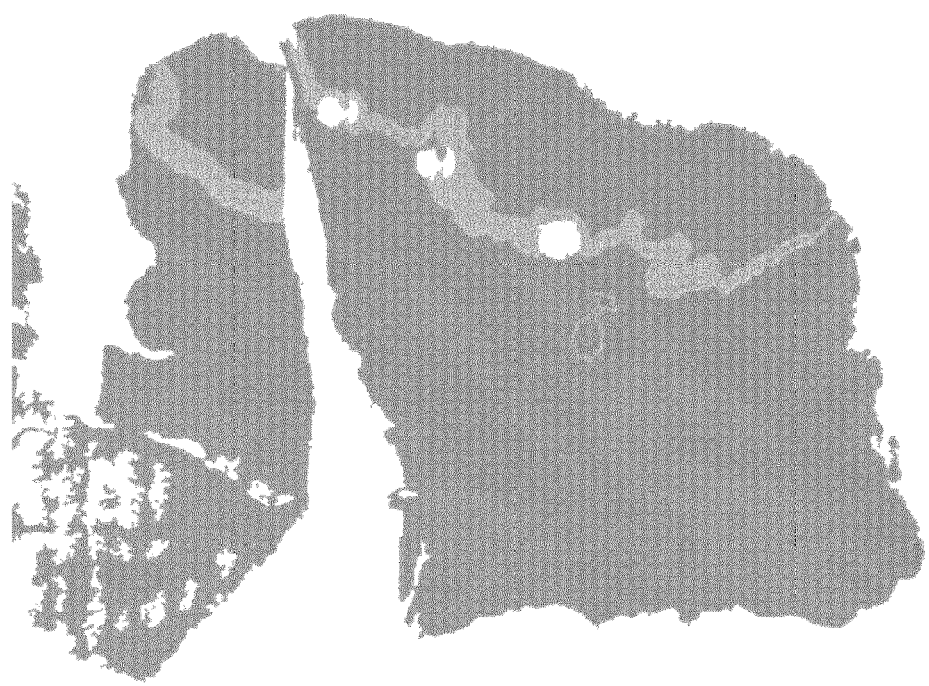
FIG. 4 is a picture showing three areas of the tissue section: Tumour at the top, healthy tissue at the bottom and invasive margin between these areas.
Figure 5:
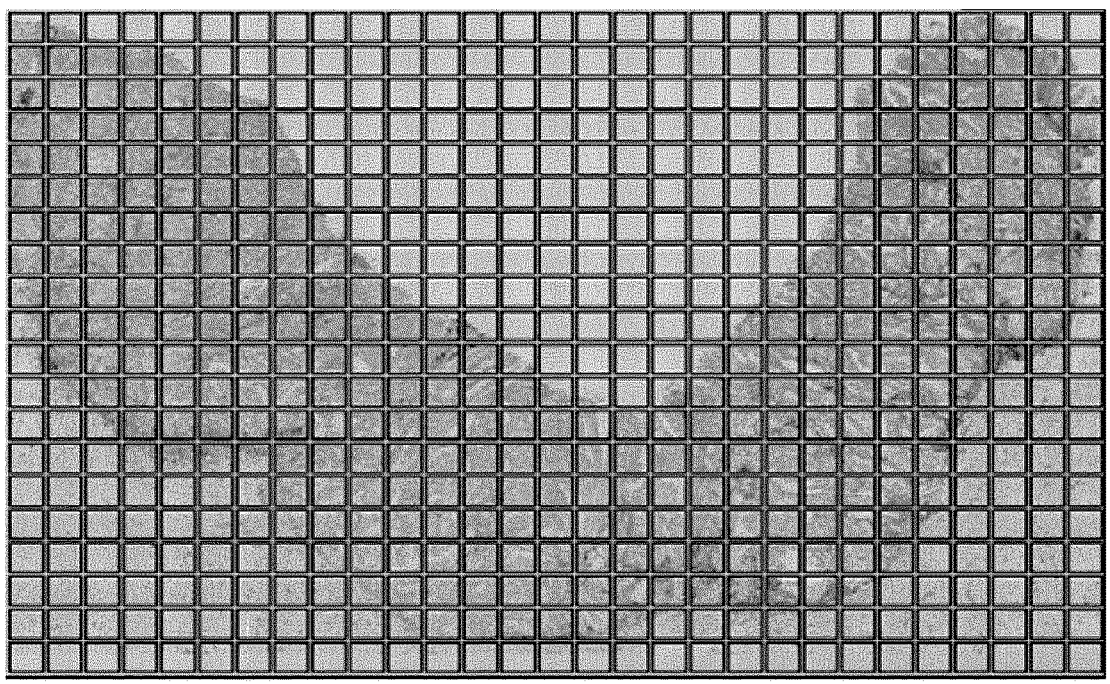
FIG. 5 shows a size reference grid with square shaped units, adapted to the size of the tumour (tumour and invasive margin) analyzed. The tumour is in grey and is V shaped.
Figure 6:
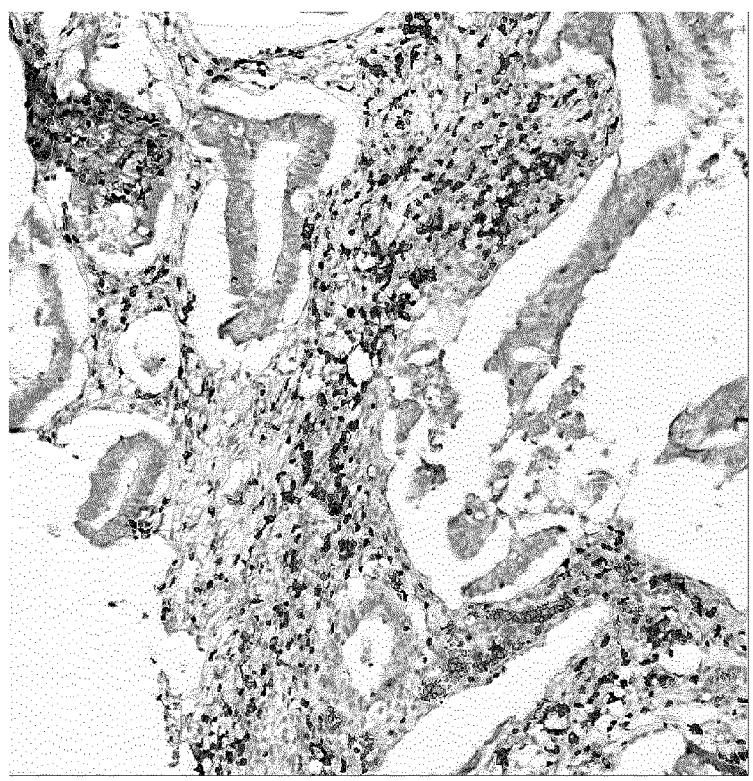
FIG. 6 is a picture of a typical unit. Black dots correspond to stained cells, i.e. cells containing the marker.
Figure 7:
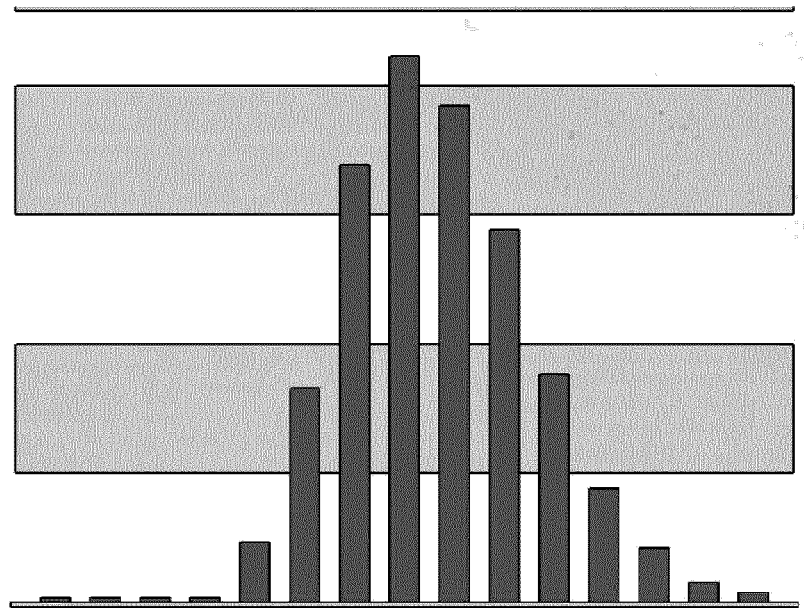
FIG. 7 displays a representative curve showing the quality of staining obtained for one grid unit as a function of intensity of the brown staining for all positive cells detected by the software. The assessment of quality of staining is preferably implemented on all the units of a tissue section.
Figure 8:
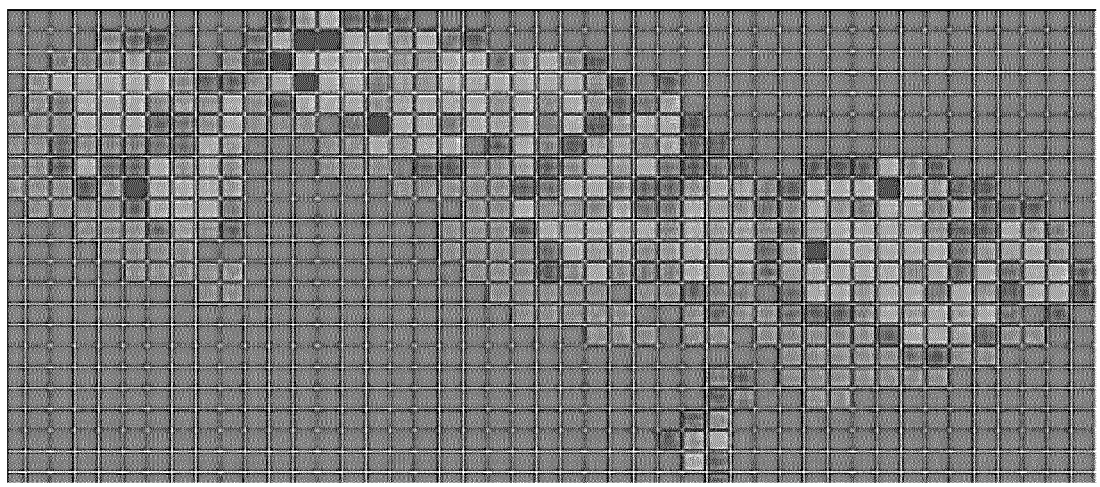
FIG. 8 is a picture of the tumour. According to the number of stained cells in a given unit, a more or less dark colour has been allotted by the software.
Figure 9:
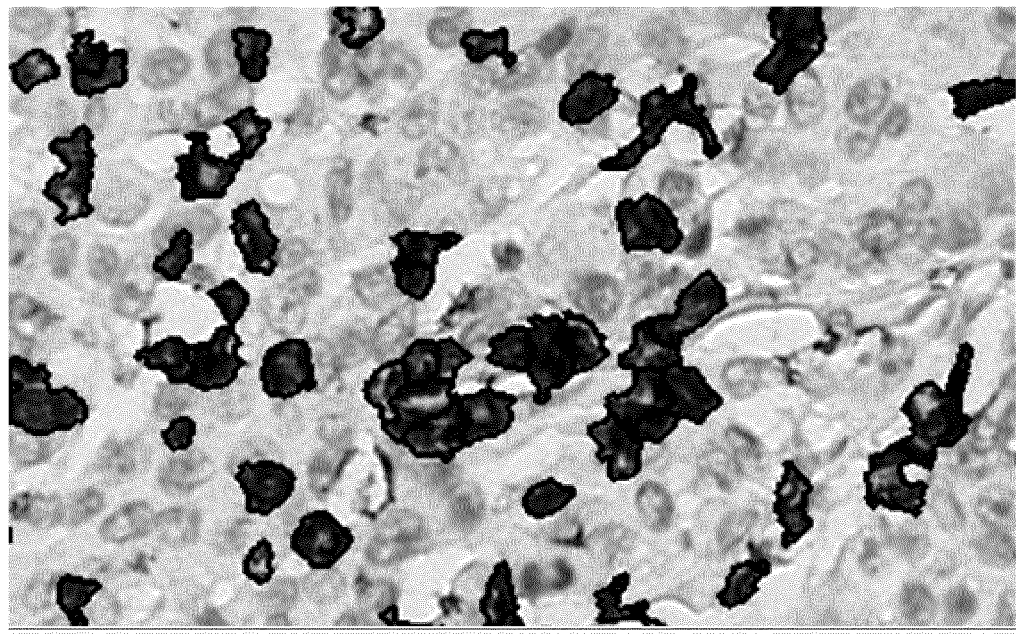
FIG. 9 is an enlargement of a part of FIG. 6, wherein stained cells (in black) are better evidenced.
Figure 10:
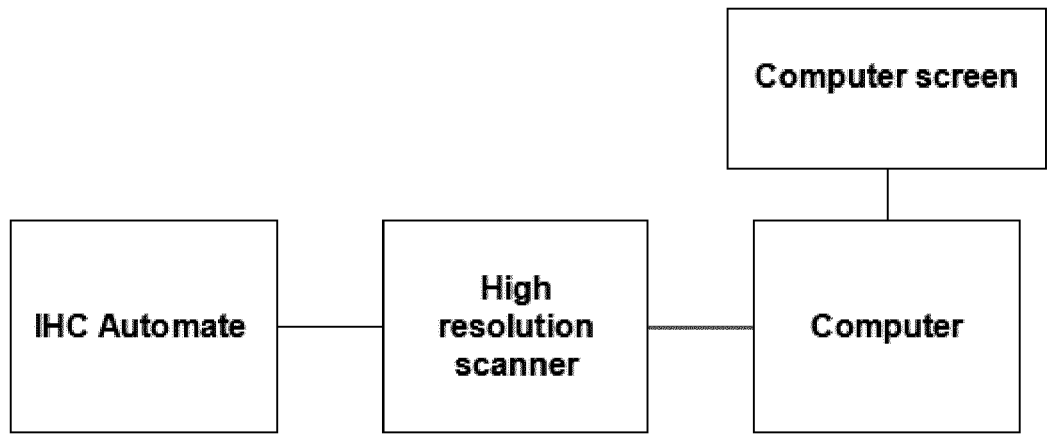
FIG. 10 is a block diagram of a system for carrying out the invention
Figure 11:
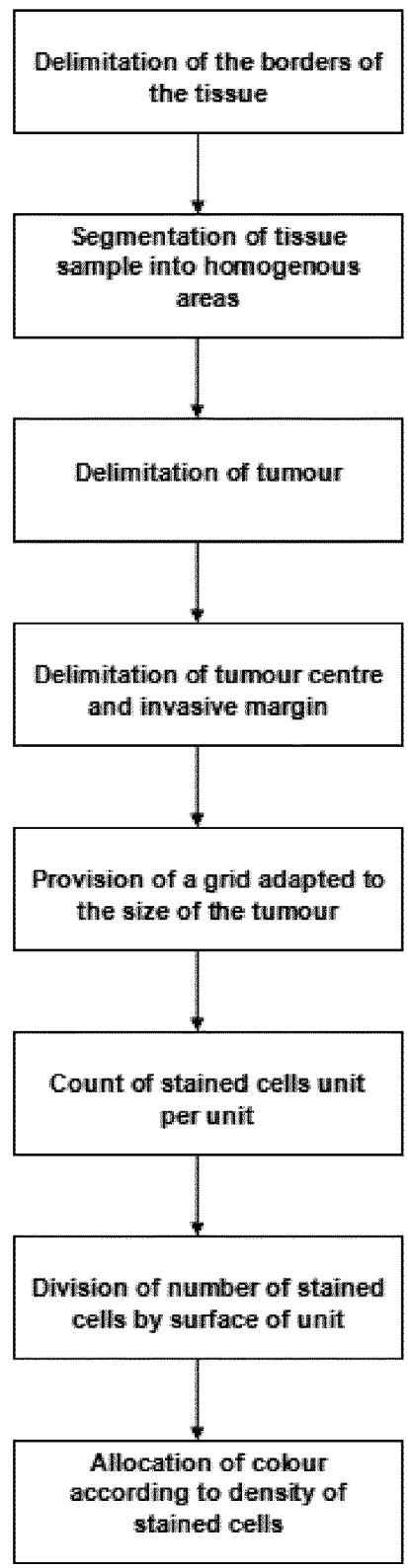
FIGS. 11 and 12 are programming flow diagrams illustrating one example of a procedure for implementing steps of the method according to the invention.

One procedure according to the invention for obtaining a picture showing three areas of a tissue section of a tumour is shown in FIG. 10.

The procedure begins at step 10 "delimitation of the borders of the tissue" when a digital picture of a slide is analyzed for obtaining the boundaries of the tissue section.

Then, in step 12 "segmentation of tissue sample into homogenous areas", parameters such as colour of the area, intensity of counterstaining, density of the area for nuclei, compactness, emptiness, tissue density, granulosity, shape, size of detected elements and area, or several of these parameters are analyzed and the tissue section is divided into homogenous areas of similar properties according to said parameters. Usually for a tissue sample having a surface of about 1-10 cm$^2$, 100 to 10000 areas, typically 2000 to 4000 homogenous areas are obtained.

Then, in step 14 "delimitation of tumour", the computer (or a skilled person, usually a medical doctor), digitally delimits the tumour and the invasive margin in view of the result of step 12 taking into account parameters such as size and morphology of cell nucleus, colour of cell nucleus, etc. When a skilled person implements this step, for example he can use the mouse of the computer or a stylus therefor.

Then, in step 16 "delimitation of tumour centre and invasive margin", the tissue section is divided into three areas: Tumour, healthy tissue and invasive margin. The software defines an intermediate area named "invasive margin" between healthy tissue and tumour, for example 500 μm wide on each side of the boundary of the tumour, therefore having a width of 1 mm. In fact long studies made by the inventors have evidenced that a width of 1 mm was the most representative of the invasive margin.

In step 18 "provision of a grid adapted to the size of the tumour", a rectangular grid adapted to the size of the tumour, and invasive margin is created. The rectangular grid is composed of square shaped units having typically sides of 500 to 1000 μm in length, preferably about 800 μm.

In step 20 "count of stained cells unit per unit", stained cells are counted taking into account parameters such as colour of cells, expected size of a single cell, shape of cells, or intensity of staining.

In step 22 "division of number of stained cells by surface of unit", the number of stained (positive) cells is divided by the surface area of a unit (for example 0.64 10$^{-6}$ m$^2$ for a square having sides of 800 μm in length. A density of stained (positive) cells by surface unit is thus obtained.

In step 24, "Allocation of colour to each unit according to density of stained cells", the software allocates a colour to each unit as a function of the density, for example from light yellow to dark red.

As previously mentioned, this procedure may be implemented separately for each marker if more than one marker is used in the method. For example procedure is implemented for CD3 cells and then for CD8 cells.

Figure 12:
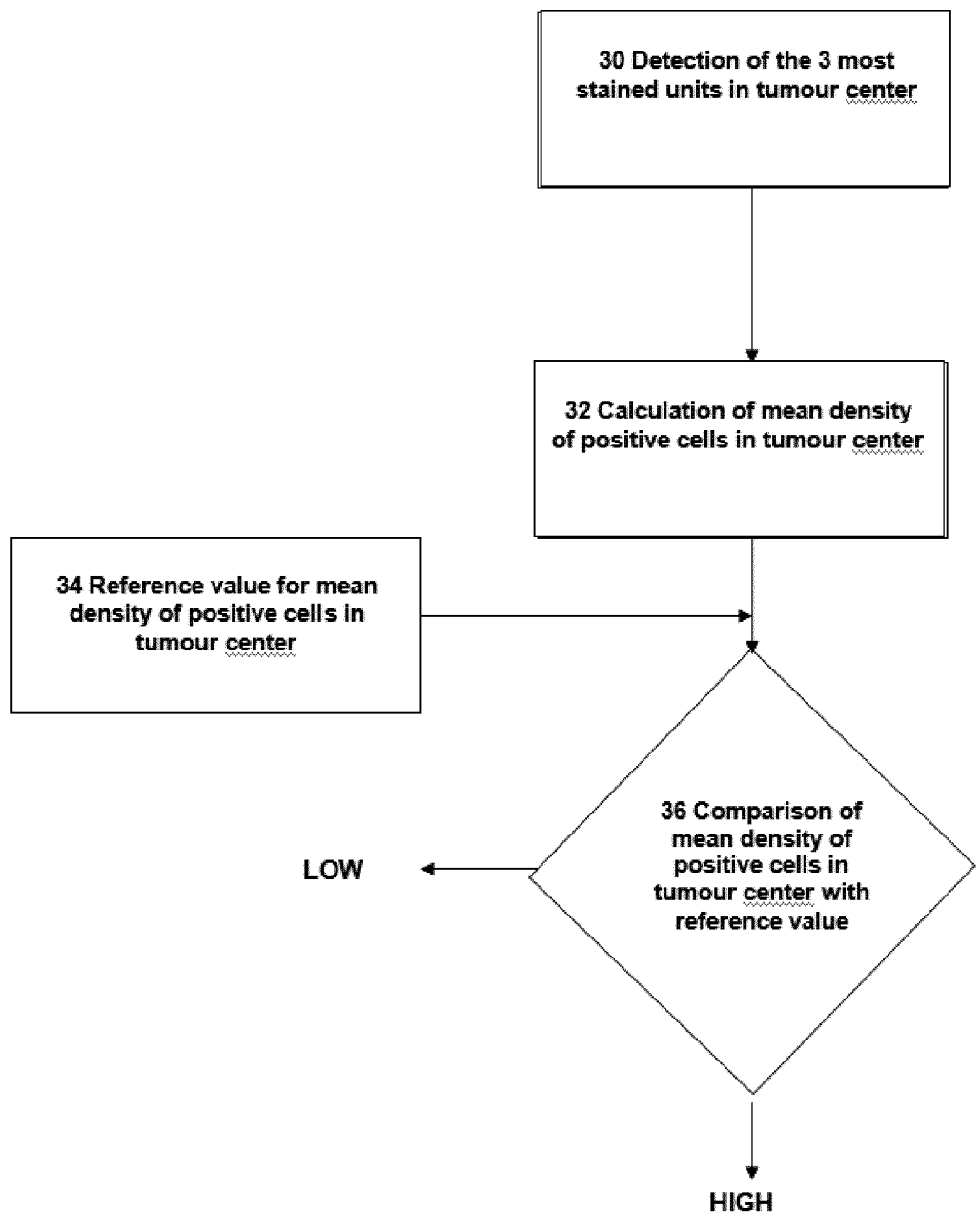
Figure 13:
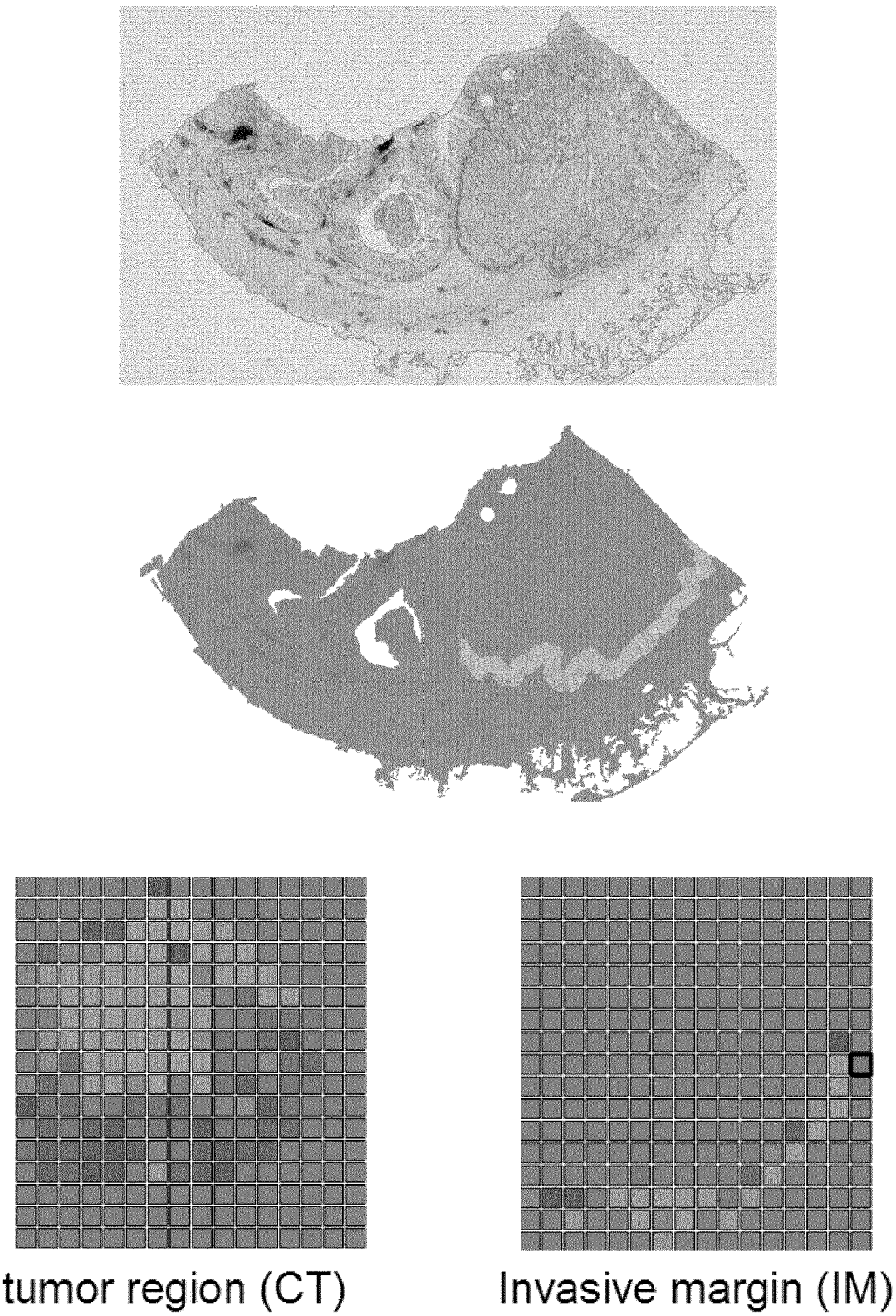
FIG. 13 illustrates the quantification method of example 2 and particularly a detection of CD3+ cells in a tumour section (whole slide analysis of a colorectal cancer). Top drawing: boundaries of tissue sample, tumour and invasive margin next drawing the tissue section is divided into three areas: Tumour on the top right, healthy tissue on the left and bottom right and invasive margin lightest area.
Figure 14:
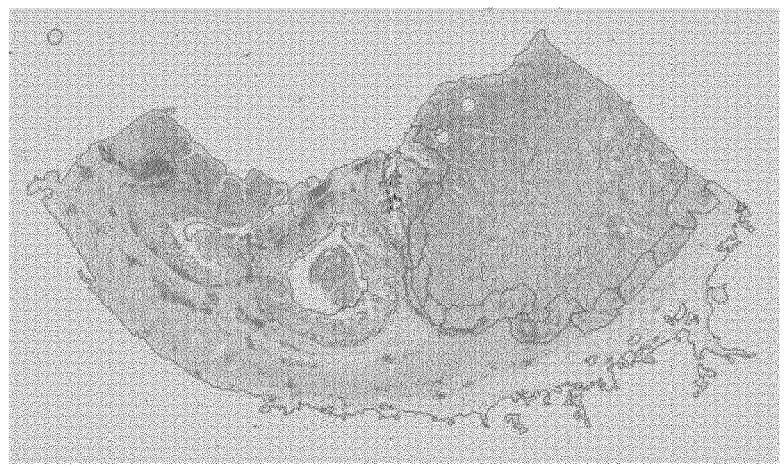
FIG. 14 illustrates the quantification method of example 2 and particularly a detection of CD8+ cells in a tumour section (whole slide analysis of a colorectal cancer). Top drawing: boundaries of tissue sample, tumour and invasive margin next drawing the tissue section is divided into three areas: Tumour on the top right, healthy tissue on the left and bottom right and invasive margin lightest area.
Figure 14:
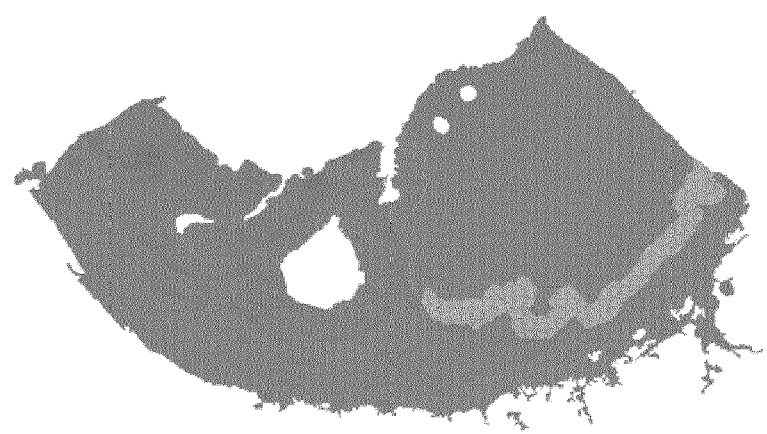
Figure 14:
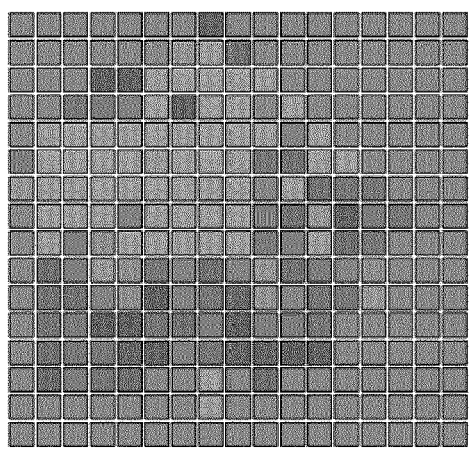
Figure 14:
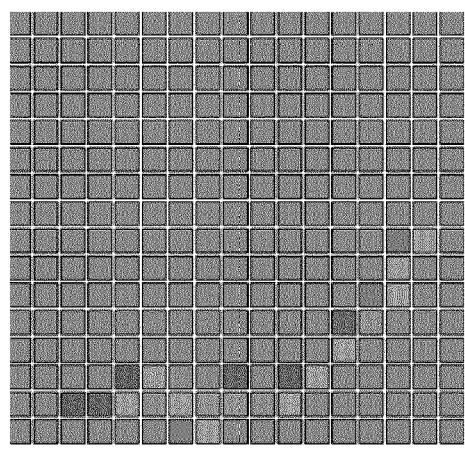

One procedure according to the invention for segregating patients into groups is shown in FIG. 12. In this example, the following combination of parameters has been selected: A mean density of positive cells, B Three most stained units and C Tumour regions CT and IM.

The procedure begins at step 30 "Detection of the 3 most stained units in tumour centre". "Tumour centre" is used in contrast with "tumour margin". The software detects the 3 most stained units (for example darkest red units) according to the data of step 24 above.

In step 32 "Calculation of mean density of positive cells in tumour centre", the mean density of stained (positive) cells is calculated.

In step 34 "Reference value for mean density of positive cells in tumour centre", the threshold/reference value is provided by a data base containing the threshold/reference value for the said combination of parameters and the said marker. The data base preferably comprises the threshold/reference value for each combination of parameters and each marker.

In step 36 "Comparison of mean density of positive cells in tumour centre with reference value", the value of step 32 is compared to the threshold/reference value of step 34 and provides the required information. If the value of step 32 is above the threshold/reference value of step 34, the sample is considered as "HIGH" for example, as "LOW" in the opposite case.

The procedure is implemented for example for two markers and for Tumour regions CT and IM.

A score may be obtained from said information and the expected survival of a patient may be assessed in a reliable way because human intervention and assessment is limited to the minimum.

EXAMPLES

Example 1: Manufacture of Stained Slides of Tumour Tissue

Two tissue paraffin sections of 4-microns of the tumour block selected were made and deposited in deionized water on microscope slides (Superfrost-plus slides) for immunohistochemistry. Tissue paraffin sections was dried at room temperature and incubated in a 56° C.-58° C. oven overnight.

Immunostainings was performed with IVD certified antibodies for CD3 and CD8 (CONFIRM CD3 (2GV6, Ventana) and CD8 (C8/144B; Dako)). The associated protocol contained the key steps of blocking, epitope recovery, and detection. A modified Mayer's haematoxylin intended for staining cellular nuclei on slides was applied (Hematoxillin II, Ventana) to optimally detect the stained cells with the dedicated software. The Protocol used with the Benchmark XT automate (Roche-Ventana) was:

| Antibodies | CD8 | CD3 VMS |
|---|---|---|
| Antibodies dilution | 1/5O | pre diluted |
| Antibodies final concentration | 3 μg/ml(1/5O) | 0.4 μg/ml(pre diluted) |
| Antibodies retrieval | CC1 pH 8-6O min | CC1 pH 8-6O min |
| Antibodies incub. | 32 mn 37° C. | 20 mn 37° C. |
| staining | Ultraview TM DAB | Ultraview TM DAB |
| Counter staining | 4 mn | 4 mn |
| Bluing reagent | 4 mn | 4 mn |

CC1 is a tris-based buffer with a slightly basic pH. The Primary Antibody Diluent for CD8 was K004 (Cliniscences).

Scanning Stained Slides of Tumour Tissue for Obtaining Digital Pictures

A numerization of the slides into digital image was performed with a scanner (NanoZoomer 2.0-HT, Hamamatsu) in a 20× mode. The format of the digital image was compatible with the Definiens Developer XD image analysis system. To avoid inhomogeneous colors on the scanned images, a calibration was performed for the white Balance, Dark & Bright and for the shading.

Example 2: Analysis of Stained Slides by Software Treatment

A pathologist has uploaded the digital image of each immunohistochemistry for CD3 and CD8 and starts the analysis with a dedicated image analysis software (Definiens Developer XD)

the semi-automatic procedure contains a step for:

the automatic detection of the tissue, the automatic segmentation of the tissue into units, the manual removal of the artifacts (folds, tears, bubbles, . . . ), the manual selection of the tumour area by the pathologist, using a brush as digital tool, the automatic detection of the invasive margin, the automatic detection of the stained cells in each unit of the tumour, the analysis of the graph for the distribution, the mean and the median of the staining intensities of positive cells detected by the software, in order to validate the immunostaining and the quantification of stained cells; this analysis is implemented on each unit, on all the units of the tissue section, the values and the distribution of the staining intensities is compared to a reference value respectively for CD3 and CD8; if the staining intensities have similar values (same value more or less about 20%), the sample tissue is considered as accurately stained; an example is given hereafter, the identification and validation of the three most infiltrated units in each tumour region (CT and IM), the calculation of the mean density of the three most infiltrated units in each tumour region.

CD3 IHC Analysis

| Tumour region (CT) | Unit#1 cells/mm² | Unit#2 cells/mm² | Unit#3 cells/mm² | mean 3 units CT region (cells/mm²) |
|---|---|---|---|---|
| C04H1807-13_n2 | 948.33 | 989.81 | 999.51 | 979.22 |

| Invasive Margin (IM) | Unit#1 cells/mm² | Unit#2 cells/mm² | Unit#3 cells/mm² | mean 3 units IM region (cells/mm²) |
|---|---|---|---|---|
| C04H1807-13_n2 | 2349.21 | 2379.06 | 2567.92 | 2432.06 |

CD8 IHC Analysis

| Tumour region (CT) | Unit#1 cells/mm² | Unit#2 cells/mm² | Unit#3 cells/mm² | mean 3 units CT region (cells/mm²) |
|---|---|---|---|---|
| C04H1807-13_n1 | 680.37 | 780.87 | 911.66 | 790.97 |

| Invasive Margin (IM) | Unit#1 cells/mm² | Unit#2 cells/mm² | Unit#3 cells/mm² | mean 3 units IM region (cells/mm²) |
|---|---|---|---|---|
| C04H1807-13_n1 | 1256.62 | 1540.49 | 2416.79 | 1737.97 |

To determine if the patient is Hi or Lo for each marker in each tumour region, the mean densities of the most infiltrated 3 units are compared with the mean density of the optimal threshold, previously defined in the study of the referent cohort.

In the referent cohort of clinically localized colorectal cancers (UICC TNM stage I-II) the optimal threshold to discriminate the patients for the disease free survival are

| Optimal threshold | CT Cells/mm² | IM Cells/mm² |
|---|---|---|
| CD3 | 967 | 1163 |
| CD8 | 406 | 649 |
| CD45RO | 1548 | 1303 |

For the case analyzed, the tumour is

Hi/Hi for CD3

Hi/Hi for CD8

Consequently, the Immunoscore is 1-4

Example 3: Example of Calculation of an Optimal Threshold Value According to the Associated the P Values for Disease Free Survival (Log Rank Tests)

Calculation of the p value for disease free survival (Log rank tests) For each value from 20 to 2000 CD3+ cells/mm², the number of patients (thus providing patients groups) having a density of CD3+ cells in the tumour (CT region) (circles dots on bottom curve) less than said value was determined.

The p value for the Log rank tests comparing patients groups for each threshold value from 20 to 2000 CD3+ cells/mm² in the tumour (circle dots and corresponding curve) was calculated.

Figure 15:
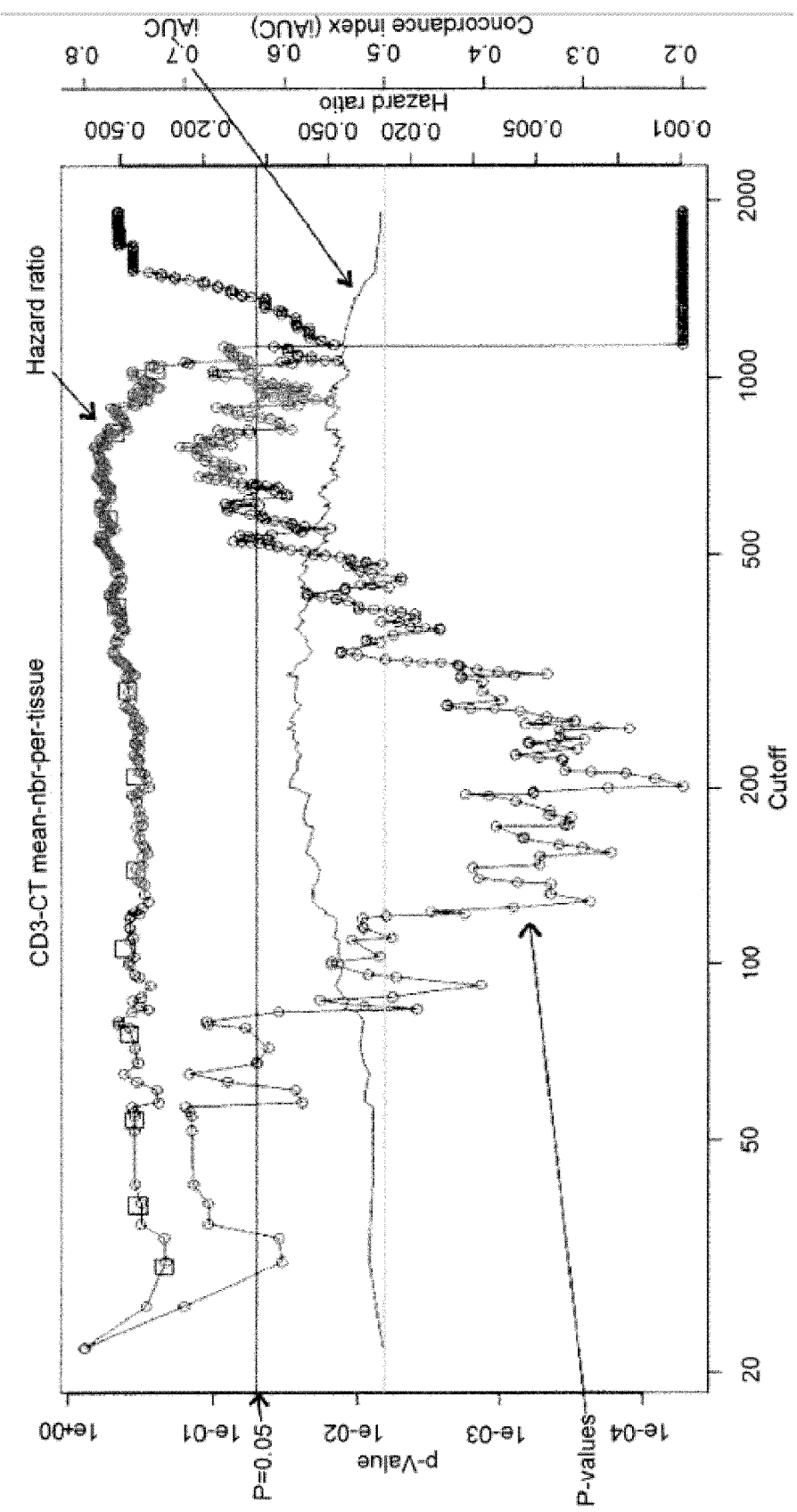
FIG. 15 illustrates a calculation of an optimal threshold value according to the associated the p values for the disease free survival (Log rank tests) and shows p values versus a density of 20 to 2000 CD3+ cells/mm$^2$.
Figure 19:
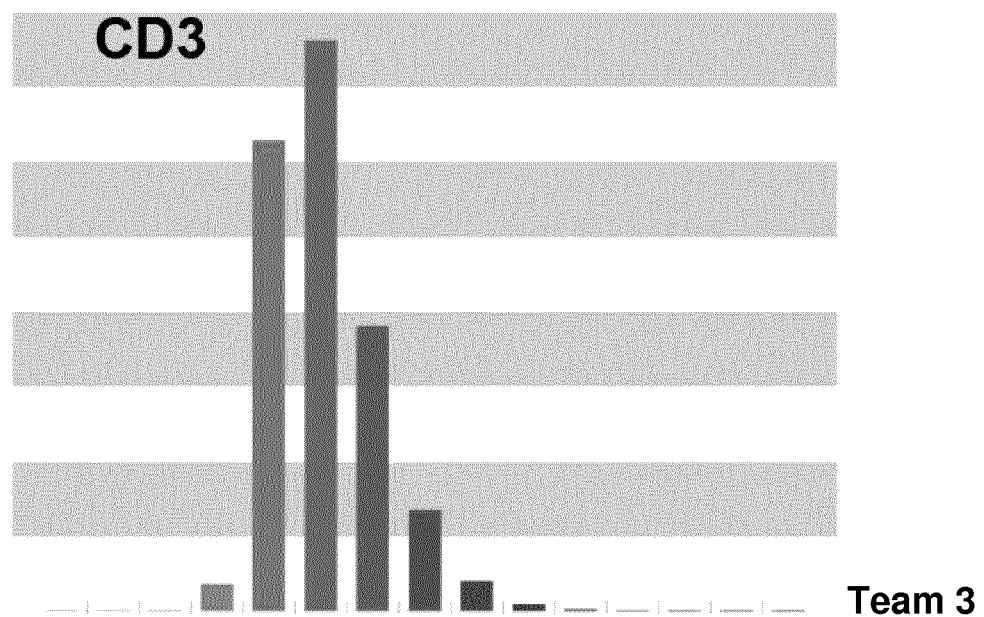

The results are given on FIG. 15.

The X-axis represents cells densities expressed in cells/mm², the Y-axis represents Log rank P-values (circle dots and corresponding curve at the bottom of the figure). The hazard ratio (square dots and corresponding curve) and iAUC concordance index (fine curve) are also represented.

Patients are categorized as "Lo" (below a given cut-point), and as "Hi" (above this cut-point). Values between 20 and 2000 cells/mm² are tested in this example. For example, for the value 100 cells/mm², patients with less than 100 CD3+ cells/mm² are in the "Lo" group, and patients with 100 or more CD3+ cells/mm² are in the "Hi" group. Kaplan Meier curves are plotted comparing Hi and Lo patients, and Log rank P-value are calculated (P=0.01, in this example).

The results show (see FIG. 15) that values between 70 and 700 cell/mm2 are significant for CD3+ in the tumour (round plots) (P<0.05). The optimal P-value threshold is provided by the value corresponding to the minimal P-value, which is found in this example at 200 cells/mm². Accordingly, the optimal threshold value is set at 200 cells/mm².

An optimal threshold value may be determined using a similar approach for each marker in each tumour region, for values other than the density of positive cells.

Example 4: Repeatability and Reproducibility of Immunohistochemistry

The repeatability and the reproducibility for CD3 and CD8 Immunohistochemistry have been studied according to different methods. (criterion of the 3 most stained units).

Repeatability Method 1:

One slide of a tumour is immunostained (for CD3 or CD8) and numerized with the scanner. The digital image is analyzed 10 times with the image analysis software by a same operator (in other terms, 10 analyses of the same immunostaining are made by a same operator). The coefficient of variation (CV) is determined.

Results:

CD3;

The CV for the CT region is 3.20%.

The CV for the IM region is 7.11%.
The CV for the analysis of the tumour (CT and IM) is 5.16%.
 CD8;
The CV for the CT region is 1.88%.
The CV for the IM region is 3.07%.
The CV for the analysis of the tumour (CT and IM) is 2.48
 Repeatability Method 2:
 Four tumour samples are analyzed. For each tumour sample, four adjacent slides are performed. The slides are immunostained (for CD3 or CD8) in the same experiment and numerized with the scanner in a same run. The digital images are analyzed with the image analysis software in a same run by a same operator. The coefficient of variation (CV) is determined for each IHC (CD3 or CD8) between adjacent slides.
 Results:
 CD3; Tumour #1-4
The CV for the CT region is 5.41%.
The CV for the IM region is 10.59%.
The CV for the analysis of the tumour (CT and IM) is 8.00%.
 CD8; Tumour #1-4
The CV for the CT region is 8.73%.
The CV for the IM region is 9.09%.
The CV for the analysis of the tumour (CT and IM) is 8.91%.
 Reproducibility method 1:
 One slide of a tumour sample from a TissueMicro Array (TMA) is analyzed. —The slide is immunostained (for CD3 or CD8) and numerized with a scanner. —The digital images is analyzed with the image analysis software in 12 runs for CD3 and 24 runs by a same operator (in other terms, 12 analyses of the same immunostaining are made by a same operator).
 The coefficient of variation (CV) is determined.
 Results:
 CD3; The CV for the TMA spot is <1%.
 CD8; The CV for the TMA spot is <1%.
 Reproducibility Method 2:
 One slide of a tumour sample is immunostained (for CD3 or CD8) and numerized with the scanner. The digital image is analyzed 10 times with the image analysis software by two operators. The coefficient of variation (CV) is determined between both operators.
 Results:
 CD3;
The CV for the CT region is 3.42%.
The CV for the IM region is 7.03%.
The CV for the analysis of the tumour (CT and IM) is 5.23%.
 CD8;
The CV for the CT region is 2.72%.
The CV for the IM region is Not Applicable (no detectable IM).
The CV for the analysis of the tumour (CT) is 2.72
 Reproducibility Method 3:
 Two tumour samples are analyzed. For each tumour sample, 5 adjacent slides are performed (C1-05). The slides are immunostained (CD3 and CD8) in different runs and numerized in different runs. The digital pictures are analyzed with the image analysis software by two operators (operator #1 for slides C1, C3 and C5; operator #2 for slides C2 and C4). The coefficient of variation (CV) is determined for each IHC (CD3 and CD8) between both investigators for adjacent slides.
 Results:
 CD3;
The CV for the CT region is 17.89%.
The CV for the IM region is 5.37%.
The CV for the analysis of the tumour (CT and IM) is 11.68%.
 CD8;
The CV for the CT region is 14.90%.
The CV for the IM region is 8.71%.
The CV for the analysis of the tumour (CT and IM) is 2.72

Example 5: Detailed Examples of Implementation of Quality Control of Immunostaining for CD3 and CD8

10 units immunostained for CD3 and CD8 in accordance with example 1 were randomly selected. The mean intensities of the units+/−1 SD were determined.

The mean values obtained are: CD3: 239+/−43 (range: 282-196), CD8: 217+/−44 (range: 261-173). Said values are considered as reference values for validating the quality of immunostaining of each sample of a given patient. The above ranges correspond to a difference of more or less 20% from the reference mean value. The man skilled in the art understands that for various reasons, the tolerance threshold may be widened (for example more or less 22% or 25%), or preferably narrowed (for example more or less 5%, 8%, 10%, 15%).

Team 1

10 units immunostained for CD3 in accordance with example 1 were randomly selected. The mean intensities of the units+/−1 SD were determined. The result obtained is: mean=234+/−64. The histogram for the distribution of the staining intensity for CD3 shows that the staining intensity of CD3 obtained is close to the reference staining intensity of CD3, within the range: 282-196.

The sample is therefore considered as correctly immunostained.

The density of immune cells stained measured by team 1:CT:1795 cells/mm$^2$, IM: 2319 cells/mm$^2$ is validated.

Team 2

The same protocol was implemented by a second team working on the slide adjacent to the slide examined by team 1.

The result obtained is: mean=251+/−56, within the range: 282-196. In view of the above reference value, the sample is therefore considered as correctly immunostained.

The density of immune cells stained measured by team 1:CT:1665 cells/mm$^2$, IM: 2198 cells/mm$^2$ is validated.

The values of densities of CD3 in tumour regions [core of the tumour (CT) and the invasive margin (IM)] obtained by team 1 and team 2 for adjacent slides are indeed similar.

Team 3

The same protocol was implemented by a third team working on the other slide adjacent to the slide examined by team 1. The result obtained is: mean=148+/−27. The histogram for the distribution of the staining intensity for CD3 shows that the staining intensity of CD3 obtained is remote to the reference staining intensity of CD3 (out of the range: 282-196).

The sample is therefore considered as incorrectly immunostained.

The density of immune cells stained measured by team 3:CT:914 cells/mm$^2$, IM: 1707 cells/mm$^2$ is not validated.

The above results show that in the absence of a reference and of a quality control of immunostaining, very different and inaccurate results may be obtained.

What is claimed is:
1. A method for assessment of a number or density of immune cells in tumoral tissues comprising:

a. providing one or more immunostained slides of tissue section obtained by an automated slide-staining system, wherein each slide of tissue section is immunostained by using antibodies binding specifically to markers expressed by immune cells, b. proceeding to digitalisation of the slides of step a. by high resolution scan capture, whereby a high definition digital picture of the slide to be analysed is obtained, c. detecting the tissue section on the digital picture, d. analyzing the slide of tissue section for defining (i) a tumour (CT) and (ii) an invasive margin of the tumour (IM), e. providing a size reference grid with uniformly distributed units having a same surface, said grid being adapted to the size of the tumour to be analyzed, f. detecting and quantifying stained cells of the slide whereby the number or the density of immune cells stained of the slide is assessed, then g. checking the quality of immunostaining by comparison with a reference value, wherein the step g. of checking the quality of immunostaining comprises, for a given marker:

measuring a distribution value representative of a distribution of staining intensities of stained cells in the slide, and comparing the distribution value with the reference value, the reference value being representative of a staining intensity of stained cells of a reference tissue section having a known distribution of the given marker, the slide being correctly stained if the distribution value is within a range around the reference value and the slide being not correctly stained if the distribution value is not within the range around the reference value, and h. validating the number or density of stained immune cells of the slide assessed during step f. if the tissue section is correctly stained as checked at step g., or not validating the number or density of stained immune cells of the slide assessed during step f. if the tissue section is not correctly stained as checked at step g.

2. The method according to claim 1, wherein detecting and quantifying stained cells of the slide is implemented separately in the tumour (CT) and the invasive margin of the tumour (IM).

3. The method according to claim 1, wherein the antibodies are selected from the group consisting of antibodies specific for CD3, CD4, CD8, CD20, CD45RO, and GZMB markers.

4. The method according to claim 1, wherein two or three antibodies selected from the group consisting of the following combinations: CD3+CD8, CD3+CD45RO, CD3+CD20, CD3+GZMB, CD8+CD20, CD8+GZMB, CD8+CD45RO, CD20+GZMB, CD20+CD45RO, GZMB+CD45RO, CD4+CD8, CD4+CD45RO, CD4+GZMB, CD4+CD20, and all the combinations of 3 markers among the CD3, CD8, CD20, CD45RO, CD4 and GZMB markers, are used.

5. The method according to claim 1, wherein an immunohistochemistry (IHC) automate is used for implementing step a).

6. The method according to claim 1, wherein step d) comprises analysing the slide of tissue section for defining the boundaries of (i) the tumour (CT) and (ii) the invasive margin of the tumour (IM) by software.

7. The method according to claim 1, wherein hexagonal, square or rectangular units having a surface of $10 \times 10^{-9}$ m$^2$ to $1000 \times 10^{-9}$ m$^2$ are used.

8. The method according to claim 1, wherein the assessed number or density of immune cells stained of the slide is selected from values of group A:

maximum number of stained cells
maximum density of stained cells
sum of the number of stained cells
sum of the surface of stained cells
sum of the densities of stained cells
mean number of stained cells
mean density of stained cells
maximum number of stained cells and
median of the number of stained cells.

9. The method according to claim 1, further comprising detecting cells or units according to a criterion selected from Group B:

single stained cells
stained cells in clusters containing at least 3 stained cells
single stained cells or clusters containing at least 3 stained cells
all stained cells
most stained units, wherein said most stained units are a number of units having a highest number of stained cells with respect to other units and
random units.

10. The method according to claim 1, wherein the reference value is at least one of a mean value, a median value, a minimum value and a maximum value of staining intensity of stained cells of a reference tissue section having a known distribution of the given marker.

11. The method according to claim 1, wherein the range around the reference value is from 20% below the reference value to 20% above the reference value.

12. The method according to claim 1, further comprising provision of an immune score of the tissue section, the provision of an immune score of the tissue section comprising the steps of:

for at least one tumour regions chosen between the tumour (CT) and the invasive margin (IM) of the tumour, comparing a value of the number or the density of immune cells for a given marker with a predetermined threshold value for the given marker allotting a positive quotation to the tumour region if the value of the number or the density of immune cells is above the predetermined threshold value, allotting a negative quotation to the tumour region if the value of the number or the density of immune cells is below the predetermined threshold value, determining the immune score of the tissue section based on a number of positive quotations and a number of negative quotations, wherein the immune score is a numerical value equal to the number of positive quotations allotted.

13. The method according to claim 12, wherein the steps of the provision of an immune score are performed for each of the tumour regions.

14. The method according to claim 12, wherein the steps of the provision of an immune score are performed for a plurality of markers.

15. The method according to claim 12, further comprising a step of segregating patients into groups according to their immune score, each patient being assigned to one group of patients having the same immune score.

16. The method according to claim 12, wherein the predetermined threshold value is related to a specific prognosis of progression of said cancer and/or survival of the patient and/or response to a cancer treatment.

* * * * *